United States Patent [19]
Rebre et al.

[11] Patent Number: 5,373,066
[45] Date of Patent: Dec. 13, 1994

[54] SUPERABSORBENT ACRYLIC POWDERS HAVING LOW RESIDUAL MONOMER CONTENT

[75] Inventors: Shu R. Rebre, Vincennes; Christian Collette; Sandrine Denie, both of Paris, all of France

[73] Assignee: Elf Atochem S.A., Puteaux, France

[21] Appl. No.: 104,757

[22] Filed: Aug. 12, 1993

[30] Foreign Application Priority Data

Aug. 12, 1992 [FR] France .............. 92 09961

[51] Int. Cl.$^5$ .............................................. C08F 8/06
[52] U.S. Cl. ........................... 525/387; 525/329.7
[58] Field of Search .................................. 525/387

[56] References Cited

U.S. PATENT DOCUMENTS

| | | |
|---|---|---|
| 4,745,154 | 5/1988 | Ruffner . |
| 4,783,510 | 11/1988 | Saotome .............. 525/387 |
| 4,959,061 | 9/1990 | Cabestany ............ 604/368 |

FOREIGN PATENT DOCUMENTS

| | | |
|---|---|---|
| 0441507 | 8/1991 | European Pat. Off. . |
| 2614027 | 10/1988 | France . |
| 103644/89 | 4/1989 | Japan . |

OTHER PUBLICATIONS

Chemical Abstracts, vol. 111, No. 18, Oct. 30, 1989, Columbus, Ohio; abstract No. 155076, Manufacture of Water-Absorbents Containing Low Residual Monomers, p. 50, col. 2 & JP-A-01 103 644 (Sanyo Chem. Ind. Ltd.).

*Primary Examiner*—Bernard Lipman
*Attorney, Agent, or Firm*—Burns, Doane, Swecker & Mathis

[57] ABSTRACT

Particulates of a superabsorbent partially, neutralized acrylic polymer, e.g., polyacrylic acid, having a mean particle size ranging from 100 to 500 μm, essentially monodisperse and essentially devoid of fines having a particle size of less than 100 μm, having a nonuniformly surfaced spheroidal particle morphology and containing less than 50 ppm of residual monomer, well suited for a variety of hygienic applications, are prepared by (i) polymerizing a suspension of an acrylic monomer charge I in an organic medium and producing a suspension of acrylic polymer gel particles, (ii) next absorbing a second acrylic monomer charge II into the gel particles, (iii) polymerizing in the gel particles the second acrylic monomer charge II, (iv) azeotropically dehydrating the acrylic polymer particulates thus obtained, (v) then treating the dehydrated particulates with hydrogen peroxide, and (vi) drying the superabsorbent particulates thus treated.

11 Claims, No Drawings

SUPERABSORBENT ACRYLIC POWDERS HAVING LOW RESIDUAL MONOMER CONTENT

CROSS-REFERENCE TO COMPANION APPLICATIONS

Our copending applications Ser. Nos. 08/104,716 and 08/104,756, both filed concurrently herewith and incorporated by reference herein, and assigned to the assignee hereof.

BACKGROUND OF THE INVENTION

1. Field of the Invention

The present invention relates to the production of superabsorbent acrylic polymer powders capable of absorbing large amounts of water or aqueous fluids and which are well suited for a variety of hygienic applications.

2. Description of the Prior Art

It is known to this art to produce polymer particulates having a high capacity for water absorption by inverse suspension polymerization of ethylenically unsaturated monomers, more particularly of acrylic monomers. The powders which are thus obtained swell greatly in the presence of water, providing gels of high mechanical strength. These properties are useful, inter alia, for the manufacture of sanitary appliances, e.g., sanitary napkins, for absorption and retention of body fluids.

Such polymers, however, contain not insignificant amounts of residual monomer. This presents a serious problem because these monomers are toxic or at least irritating or damaging to mucous membranes and human skin. Various more or less satisfactory solutions have been proposed to this art for reducing the residual monomer content of the hydrophilic acrylic monomers, for example treatment with isopropanol (EP-0,262,380, Cassella), with hydroxylamine (U.S. Pat. No. 4,929,717, Stockhausen), with an amino acid such as lysine (U.S. Pat. No. 4,766,173, Nalco) or with azo compounds or peroxides (JP-89/103,644, Sanyo). The latter, in particular, relates that the monomer content can be reduced to a level of 500 ppm either by introducing an oxidation-reduction couple into the mass undergoing polymerization, or by treating the polymer formed, but prior to its final drying, with 0.01 to 100 ppm of hydrogen peroxide relative to the polymer (expressed as dry weight), 0.01 ppm being a lower limit below which no significant effect on the residual monomer content is observed, and 100 ppm being an upper limit which cannot be exceeded without adversely affecting the absorption capacity of the final product.

One significant improvement in the production of such absorbent powders is described in EP-0,441,507, comprising polymerization of the acrylic monomer in at least two separate stages. In a first discrete stage, an inverse suspension polymerization is carried out in conventional manner, such polymerization resulting in the formation of a gel. In a second stage, a fresh monomer charge is absorbed into this gel and polymerization thereof is initiated within the actual gel formed previously. If appropriate, this absorption/polymerization sequence can be repeated. In this fashion, polymeric resins are prepared having a particle size which is appreciably larger than the resins obtained via single inverse suspension polymerization. Their degree or extent of swelling in the presence of water, elastic modulus, plasticity and resistance to collapse under pressure of the gel, are also appreciably improved.

SUMMARY OF THE INVENTION

A major object of the present invention is the provision of an improved process for the preparation of superabsorbent acrylic powders via two-stage suspension polymerization, the residual monomer contents of which being reduced to a level as low as 50 ppm.

Briefly, the present invention features the two-stage suspension polymerization of acrylic monomers, including a final sequence of isolation of the polymer particulates which comprises first removing water therefrom via azeotropic distillation, next treating the dehydrated particulates with hydrogen peroxide and then completing the drying thereof.

DETAILED DESCRIPTION OF PREFERRED EMBODIMENTS OF THE INVENTION

More particularly according to the present invention, it has now unexpectedly been determined that the treatment with hydrogen peroxide must be intermediate the azeotropic distillation and the final drying. Otherwise, the markedly reduced levels of residual monomer cannot be attained.

In the two-stage polymerization according to the invention, nonionic surfactants are generally used to formulate the suspension, such as the esters of fatty acids with sorbitan, with polyglycerol or with sucrose, or the Polyoxyethylene-alkylphenyl ethers. However, it is industrially very advantageous to carry out the absorption phase of the multi-stage process without having to cool the reactor to any great extent. Conducting this absorption at temperatures of 35° to 45° C. very significantly improves the economics of the process, but for this it is necessary to employ special surfactants for the stage of the initial polymerization in inverse suspension. These are either surfactants of the polyethylene glycol/dodecyl glycol block copolymer type, formed from a polyethylene glycol chain provided at one and-/or the other of its ends with a plurality of hydrophobic residues comprising dodecyl glycol radicals and especially polyethylene glycol/dodecyl glycol block copolymers. It is thus possible to carry out the absorption of the second charge of monomer into the polymeric gel formed in the first instance, at temperatures on the order of 35° C. Surfactants of a polymerizable type can also be used, corresponding to the general formula:

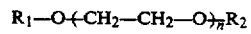

$$R_1-O-(CH_2-CH_2-O)_n R_2$$

wherein $R_1$ is a hydrocarbon having at least 9 carbon atoms, $R_2$ is a polymerizable functional group, or an acryloyl, methacryloyl or maleoyl radical, and the degree of condensation n in respect of the ethylene oxide ranges from 30 to 70. These surfactants permit conducting the stage of adsorption of the second charge of monomer into the gel at a temperature of 45° C. The maleic acid monoester of nonylphenyl oxyethylenated with 50 molecules of ethylene oxide is a preferred surfactant of this type.

It has also been shown to be desirable to vary the neutralization of the aqueous phases of acrylic monomer to be polymerized, i.e., by first using a monomeric acrylic acid which is over-neutralized relative to the degree of neutralization desired for the final polymer, and, for the phase to be polymerized after absorption into the gel thus formed, a monomeric acrylic acid which is underneutralized.

The product of this process is a powder no longer comprising smooth spheres, but of spheroidal particles having an irregular surface, the shape of which is not dissimilar from that of truffles, and having a large particle size ranging from 100 to 500 μm, with the proportion of fines that pass through a 100 μm screen being very low, in each instance using less than 0.5% by weight. This is desirable at the manufacturing level because the process directly produces large particles and only these can be used for the usual hygienic applications. Also, a post-agglomeration sequence, thus, is not required.

Moreover, the irregular geometry of the particles ensures better fixation into a fibrous medium or matrix, and, hence, greater ease of processing in the production, e.g., of sanitary napkins. These products are, however, not devoid of residual monomers and it is very useful to prepare same via the process of the invention, to reduce the content of residual monomer to 50 ppm or less. The powders thus produced are spheroidal particles, having an irregular surface, of polyacrylic acid neutralized to a degree of from 65% to 95% and having a mean diameter ranging from 100 to 500 μm, with less than 0.5% passing through a 100 μm screen, and a residual monomer content which is at most 50 ppm.

The amounts of hydrogen peroxide used advantageously range from 0.08% to 0.19% by weight relative to the dry polymer. The hydrogen peroxide is introduced after dilution, preferably to a hydrogen peroxide concentration of 1% to 20%, into the reactor after the azeotropic dehydration and before the final drying of the polymer.

In order to further illustrate the present invention and the advantages thereof, the following specific examples are given, it being understood that same are intended only as illustrative and in nowise limitative.

In said examples below, the following sequences are carried out:
 (a) preparation of the solvent phase;
 (b) preparation of the aqueous monomer phase (charge I);
 (c) suspending the monomer phase I in the solvent phase and conducting the polymerization I;
 (d) preparation of the second aqueous monomer phase (charge II);
 (e) absorption of monomer charge II into the polymer gel I conducting the polymerization II; and
 (f) isolation of the final polymer.

EXAMPLE 1 (Comparative)

In this example a polyacrylic acid neutralized to the extent of 75% was prepared in accordance with the usual process of inverse suspension polymerization of the prior art; accordingly, it comprised neither sequence (d) nor sequence (e).

Sequence (a)

Into a one-liter reactor equipped with means for introducing solid or liquid reactants, a propeller stirrer or another stirrer, a temperature probe, a system for flushing with neutral gas and heating and cooling means, 1.38 g of polyethylene modified with maleic anhydride, a product marketed by Mitsui Petrochemical Industries under the trademark Hi-Wax 1105A, and 0.92 g of sucrose distearate/tristearate were dissolved in 376 g of heptane at about 80° C., with stirring at 325 rpm.

Sequence (b)

Separately, 92 g of an 80% by weight aqueous solution of acrylic acid were neutralized, while maintaining the temperature below 30° C., with 141.6 g of 21.66% concentration sodium hydroxide solution. Then, 0.276 g of hydroxyethylcellulose was added, followed by 11 g of a 0.95% aqueous solution of potassium persulfate.

Sequence (c)

While continuing to stir the reactor at 400 rpm and flushing it with nitrogen at the rate of 80 liters/minute, the previously prepared aqueous phase was introduced, small amounts at a time, and converted into inverse suspension in the heptane. The temperature was increased to 70° C. to initiate the polymerization and was maintained at this value for about 30 minutes. The temperature was then deceased to 20° C.

Final sequence (f)

First, the agglomeration of the polymer particles was carried out by adding 0.55 g of colloidal silica (Tokusil P) diluted in 45 g of heptane. The temperature was increased to 60°–70° C., with stirring at 1,500 rpm. Thereafter, the heptane and the greater fraction of the water were removed by distillation. Then, 9.2 g of a 2% aqueous solution of ethylene glycol diglycidyl ether were then added to the contents of the reactor and the drying was continued.

The powder thus obtained contained 2% of particles that passed through a 100 μm screen, and had an unacceptable acrylic monomer content of 100 ppm, due to the modest amounts of potassium persulfate employed in sequence (b).

EXAMPLE 2 (Comparative)

In this example, a polyacrylate neutralized to the extent of 75% was prepared, in accordance with the two-stage process of the prior art, namely, a first polymerization in inverse suspension, absorption and a second polymerization within the gel.

Seguence (a)

Into the apparatus described in Example 1, 0.92 g of Hi-Wax 1105A modified polyethylene and 0.736 g of sucrose distearate/tristearate were dissolved in 376 g of heptane at 80° C., while stirring at 400 rpm.

Seguence (b)

Separately, 92 g of an 80% by weight aqueous solution of acrylic acid were neutralized with 176.8 g of 17.35% sodium hydroxide solution. Then, 0.276 g of hydroxyethylcellulose was added, followed by 5.5 g of a 1% strength aqueous solution of potassium persulfate and 0.92 g of a 2% strength aqueous solution of ethylene glycol diglycidyl ether. This aqueous phase was heated to 38° C.

Sequence (c)

While continuing to stir the reactor at 400 rpm and flushing it with nitrogen at the rate of 80 liters/minute, the previously prepared aqueous phase was introduced, small amounts at a time, and was converted into inverse suspension in the heptane. The temperature was increased to 70° C. to initiate the polymerization and was maintained at this value for about 30 minutes. The temperature was then deceased to 20° C.

Sequence (d)

While the preceding operation was being carried out, 92 g of an 80% by weight aqueous solution of acrylic acid were separately neutralized with 176.8 g of 17.35% strength sodium hydroxide solution, after which 5.5 g of a 1% strength aqueous potassium persulfate solution and 0.92 g of a 2% strength aqueous ethylene glycol diglycidyl ether solution were added. This aqueous phase, which constituted the monomer charge II, was then heated at 20° C.

Sequence (e)

Stirring in the reactor was adjusted to 800 rpm, while continuing the flushing with nitrogen at 80 liters/minute. Charge II was introduced, small amounts at a time, after which the temperature was increased to 70° C. to initiate the second polymerization phase. The polymerization was permitted to continue for about 30 minutes.

Final sequence (f)

First, the agglomeration of the polymer particles was carried out by adding 0.55 g of colloidal silica (Tokusil P) diluted in 45 g of heptane. The temperature was increased to 60° C. -70° C., with stirring at 1,500 rpm. Thereafter, the heptane and the greater fraction of the water were removed by distillation. Then, 9.2 g of a 2% aqueous ethylene glycol diglycidyl ether solution were added to the contents of the reactor and the drying was continued.

The powder obtained contained 1% of particles that passed through a 100 μm screen and had a high free monomer content of 414 ppm.

EXAMPLE 3 (Comparative)

This is a comparative example which only differs from Example 2 in that, during the sequence (d) of preparation of the second aqueous charge of acrylic monomer, 5.5 g of 1% strength hydrogen peroxide were introduced at the same time as the potassium persulfate and the ethylene glycol diglycidyl ether.

The powder thus obtained contained 1% of particles that passed through a 100 μm screen and its free acrylic monomer content remained very high (490 ppm).

EXAMPLE 4

This example according to the invention only differs from Example 2 in that, between the dehydration stage and the drying stage of sequence (f), 0,552 g of 20% strength aqueous hydrogen peroxide were introduced at the same time as the 9.2 g of 2% strength ethylene glycol diglycidyl ether.

This produced a powder, about 1% by weight of which passed through a 100 μm screen and in which the free acrylic monomer content had now decreased to 30 ppm.

EXAMPLE 5

In this example, the advantages of producing a polyacrylic superabsorbent were demonstrated by inverse suspension polymerization, absorption and polymerization within the gel, in which the absorption of the second monomer charge had been conducted at 35° C., combined with the introduction of hydrogen peroxide between the polymer dehydration stage and the polymer drying.

Sequence (a)

Into the apparatus described in Example 1, 0.92 g of Hi-Wax 1105A modified polyethylene was dissolved in 265.6 g of heptane at 80° C., while stirring at 400 rpm.

Sequence (b)

Separately, 92 g of an 80% by weight aqueous solution of acrylic acid were neutralized with 139.4 g of a 22% strength sodium hydroxide solution. Then, 0.276 g of hydroxyethylcellulose was added, followed by 5.5 g of a 1% strength aqueous solution of potassium persulfate, 0.92 g of a 2% aqueous solution of ethylene glycol diglycidyl ether and 0.18 g of a maleate ester of nonylphenol containing 50 mol of ethylene oxide (Aerosol MEM-NP 50 marketed by Cyanamid). It will be appreciated that this emulsifier was introduced into the system in solution in the aqueous charge, which is rather unusual if it is desired to form an inverse suspension.

Sequence (c)

While continuing to stir the reactor at 400 rpm and flushing it with nitrogen at a rate of 80 liters/minute, the previously prepared aqueous phase was introduced, small amounts at a time, and was converted into inverse suspension in the heptane. The temperature was increased to 70° C. to initiate the polymerization and was maintained at this value for about 30 minutes. The temperature was then decreased to 15° C.

Sequence (d)

While the preceding operation was being carried out, 92 g of an 80% by weight aqueous solution of acrylic acid were separately neutralized with 139.4 g of a 22% strength sodium hydroxide solution, after which 5.5 g of a 1% strength aqueous potassium persulfate solution and 0.92 g of a 2% strength aqueous ethylene glycol diglycidyl ether solution were added. This aqueous phase, which constituted the monomer charge II, was then adjusted to 15° C.

Sequence (e)

The stirring in the reactor was increased to 800 rpm while continuing the flushing with nitrogen at 80 liters/minute. Charge II was introduced, small amounts at a time, after which the temperature was increased to 70° C. to initiate the second polymerization phase. The polymerization was permitted to proceed for about 30 minutes.

Final sequence (f)

A solution prepared from 1.84 g of a 2% strength aqueous solution of ethylene glycol diglycidyl ether and 0.552 g of 20% strength hydrogen peroxide was added to the contents of the reactor, after which the drying of the product was carried out.

1% of the powder thus obtained passed through a 100 μm screen. The residual monomer content of the powder was 41 ppm.

EXAMPLE 6

This example illustrates the advantages of the combination of an over-neutralization of the first monomer charge and an under-neutralization of the second charge, the use of a surfactant of the block polymer type which permitted carrying out the absorption of the second monomer charge by means of the gel formed during the first polymerization at a relatively high temperature of 35° C., and the reduction in the residual monomer content according to the invention.

Sequence (a)

Using the apparatus of Example 1, 0.92 g of Hi-Wax 1105A modified polyethylene and 0.46 g of a polyethylene glycol/dodecyl glycol block copolymer, namely, Dapral E348 marketed by AKZO (the molecule having about three dodecyl glycol radicals at one end of a methoxypolyethylene glycol backbone for about 22 ethylene glycol recurring structural units) were dissolved in 285.1 g of heptane at 80° C., while stirring at 400 rpm.

Sequence (b)

Separately, 92 g of an 80% by weight aqueous solution of acrylic acid were neutralized with 160.65 g of a 24.17% strength sodium hydroxide solution. Then, 0.276 g of hydroxyethylcellulose was added, followed by 2.75 g of a 2% strength aqueous solution of potassium persulfate and 0.92 g of a 2% strength aqueous solution of ethylene glycol diglycidyl ether.

sequence (c)

While continuing to stir the reactor at 400 rpm and flushing it with nitrogen at the rate of 80 liters/minute, the previously prepared aqueous phase was introduced, small amounts at a time, and was converted into inverse suspension in the heptane. The temperature was increased to 70° C. to initiate the polymerization and was maintained at this value for about 30 minutes. The temperature was then decreased to 42° C.

Sequence (d)

While the preceding operation was being carried out, 92 g of an 80% by weight aqueous solution of acrylic acid were separately neutralized with 135.75 g of 16.6% strength sodium hydroxide solution, after which 2.75 g of a 2% strength aqueous solution of potassium persulfate and 0.92 g of a 2% strength aqueous solution of ethylene glycol diglycidyl ether were added. This aqueous phase, which constituted the monomer charge II, was then adjusted to 15° C. The stirring in the reactor was increased to 800 rpm, while continuing the flushing with nitrogen at 80 liters per minute. Charge II was introduced, small amounts at a time, after which the temperature was increased to 70° C. to initiate the second polymerization phase. The polymerization was permitted to proceed for about 30 minutes.

Sequence (f)

After azeotropic dehydration, 0.92 g of a 2% strength aqueous solution of ethylene glycol diglycidyl ether and 0.552 g of 20% strength hydrogen peroxide were introduced into the reactor, after which the drying of the product was carried out.

The powder thus obtained essentially consisted of spheroidal particles having an irregular surface, with virtually no material passing through a 100 μm screen; the free monomer content of the powder was 45 ppm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of particulates of a superabsorbent partially neutralized acrylic polymer having low residual monomer content, comprising (i) polymerizing a suspension of an at least partially neutralized acrylic monomer charge I in an organic medium and producing a suspension of acrylic polymer gel particles, (ii) next absorbing a second partially neutralized acrylic monomer charge II into said gel particles, (iii) polymerizing in the gel particles said second acrylic monomer charge II, (iv) azeotropically dehydrating the acrylic polymer particulates thus obtained, (v) then treating the dehydrated particulates with hydrogen peroxide, and then (vi) drying the superabsorbent particulates thus treated.

2. The process as defined by claim 1, said acrylic monomer charge I having a degree of neutralization greater than that desired in the final superabsorbent polymer, and said acrylic monomer charge II having a degree of neutralization less than that desired in the final superabsorbent polymer.

3. The process as defined by claim 1, said acrylic monomer charges I and II comprising aqueous solutions of at least partially neutralized acrylic acid.

4. The process as defined by claim 3, said acrylic monomer charge I comprising from 90% to 100% neutralized acrylic acid and said acrylic monomer charge II comprising from 60% to 50% neutralized acrylic acid.

5. The process as defined by claim 4, the superabsorbent polyacrylic acid particulates thus obtained having a degree of neutralization of about 75%.

6. The process as defined by claim 1, said suspension of the acrylic monomer charge I comprising a surfactant.

7. The process as defined by claim 6, said surfactant comprising a polyethylene glycol/dodecyl glycol block copolymer.

8. The process as defined by claim 1, comprising absorbing said second acrylic monomer charge II into said gel particles at a temperature of about 35° C.

9. The process as defined by claim 6, said surfactant comprising a polymerizable compound having the general formula:

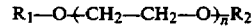

wherein $R_1$ is a hydrocarbon having at least 9 carbon atoms, $R_2$ is a polymerizable functional group, or an acryloyl, methacryloyl or maleoyl radical, and the degree of condensation n of the ethylene oxide ranges from 30 to 70.

10. The process as defined by claim 9, said polymerizable surfactant comprising the maleic ester of nonylphenol oxyethylenated with about 50 molecules of ethylene oxide.

11. The process as defined by claim 9, comprising absorbing said second acrylic monomer charge II into said gel particles at a temperature of about 45° C.

* * * * *